United States Patent [19]

Van Cleve

[11] Patent Number: 4,676,247
[45] Date of Patent: Jun. 30, 1987

[54] MULTI-POCKET THERAPEUTIC ANATOMICAL WRAP

[76] Inventor: Ardry J. Van Cleve, 11601 Audelia, Apartment #155, Dallas, Tex. 75243

[21] Appl. No.: 767,749

[22] Filed: Aug. 21, 1985

[51] Int. Cl.⁴ .............................................. A61F 7/02
[52] U.S. Cl. ..................................... 128/402; 62/530; 128/403
[58] Field of Search .................. 128/402, 403, 379; 62/530

[56] References Cited

U.S. PATENT DOCUMENTS

| | | | |
|---|---|---|---|
| 2,749,914 | 6/1956 | Braley | 128/402 |
| 3,780,537 | 12/1973 | Spencer | 128/403 X |
| 4,033,354 | 7/1977 | De Rosa | 128/402 X |
| 4,055,188 | 10/1977 | Pelton | 128/402 |
| 4,324,111 | 4/1982 | Edwards | 128/402 X |
| 4,326,533 | 4/1982 | Henderson | 128/403 X |
| 4,381,025 | 4/1983 | Schooley | 128/402 X |
| 4,527,566 | 7/1985 | Abare | 128/403 X |
| 4,556,055 | 12/1985 | Bonner | 128/402 X |

FOREIGN PATENT DOCUMENTS 1185811 3/1970 United Kingdom ................ 128/402

Primary Examiner—Anton O. Oechsle
Attorney, Agent, or Firm—Gregory M. Howison; Jerry W. Mills

[57] ABSTRACT

A thermal wrap (18) includes a outer wrap having an outer side (20) and an inner side (22). Pockets (32), (34) and (36) are disposed on the inner side of the wrap (18). The pockets are operable to receive gel packs (48), (50) and (52). The wrap has a free end (21) and a free end (23). Each of the pockets (32), (34) and (36) have a width of x. The x width is dimensioned such that the outermost pockets are disposed adjacent the medial and lateral sides of a knee of an average adult one wrap therearound. The free end (21) is designed such that it can fold over itself to prevent overlapping with the inner side of the pockets.

9 Claims, 12 Drawing Figures

U.S. Patent Jun. 30, 1987 Sheet 1 of 2 4,676,247
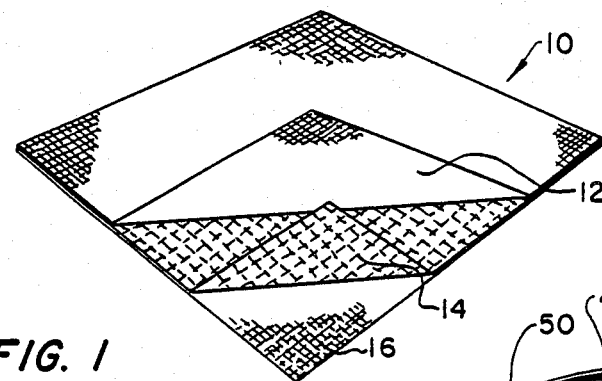
FIG. 1
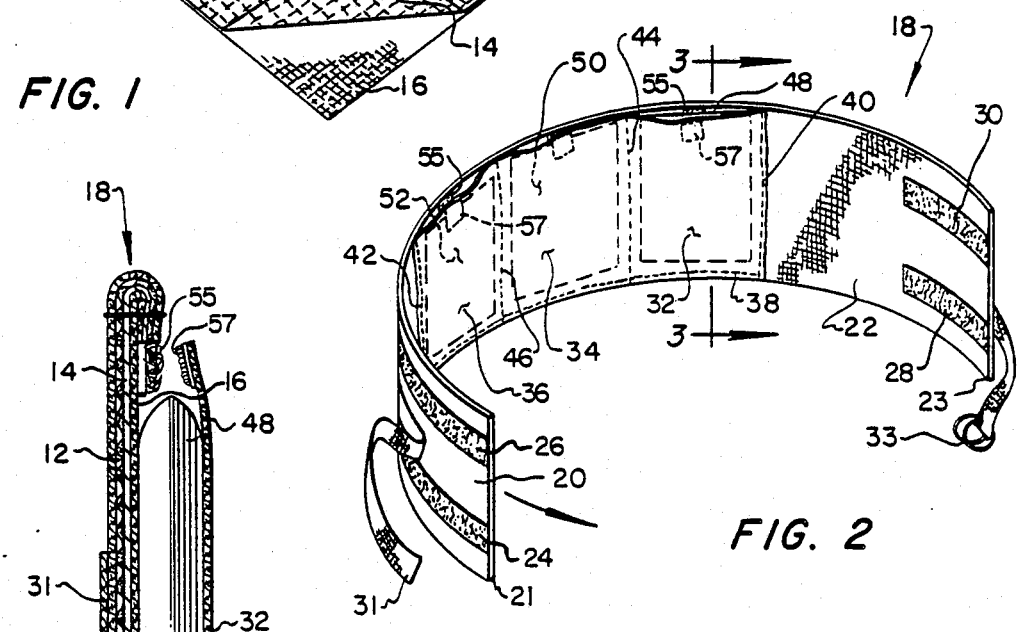
FIG. 2
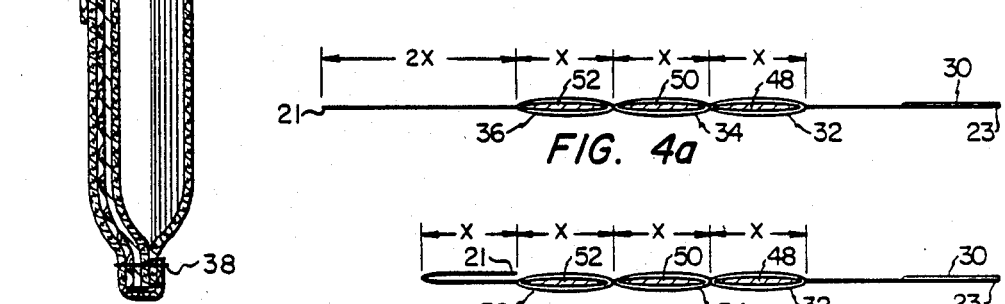
FIG. 3
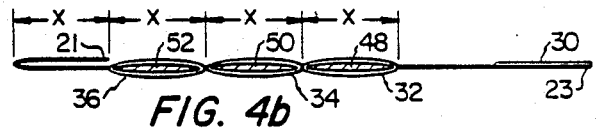
FIG. 4a
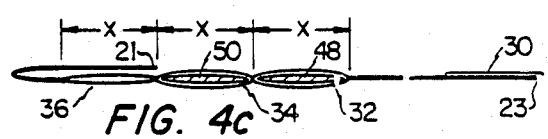
FIG. 4b
FIG. 4c
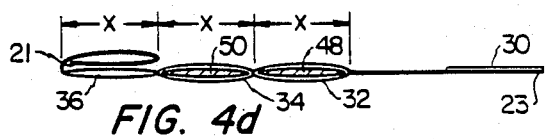
FIG. 4d

_4,676,247_

MULTI-POCKET THERAPEUTIC ANATOMICAL WRAP

TECHNICAL FIELD

The present invention pertains in general to therapeutic wraps and, more particularly, to therapeutic wraps using heat or cold in the therapeutic treatment.

CROSS REFERENCE TO RELATED APPLICATION

This application is related to patent application Ser. No. 566,284, Attorney's docket number 32270-0011, filed Dec. 28, 1983 in the United States Patent and Trademark Office.

BACKGROUND OF THE INVENTION

Treatment of injuries to joints and/or limbs normally utilizes the application of therapeutic heat or cold thereto. To facilitate this treatment, a device for retaining heat and/or cold must be placed proximate the limb and secured thereto. This is normally accomplished by utilizing a material with a relatively high specific heat that conforms to the surface profile of the portion of the anatomy to be treated. These devices normally are in the form of a gel pack that can be heated or cooled to provide an appropriate temperature gradient. Some of the disadvantages incurred in present devices is that they either are bulky and nonportable or they loose their therapeutic cooling or heating affect rapidly due to heat transfer to the injured limb and/or the atmosphere.

U.S. Pat. Nos. 3,587,578, 3,780,537, 4,055,188, 4,033,354, 3,307,554, 4,381,025, 4,326,533, 3,889,684, 4,372,318, 3,871,376, 3,900,035, 3,815,610 and 2,288,745 all disclose devices that are designed to hold a therapeutic gel pack adjacent an injured limb. These devices all have the disadvantage that they do not deliver the appropriate therapeutic effect to the appropriate anatomical areas. In addition, they are difficult to position. This is undesirable in that most existing applications of a therapeutic wrap require that the individual remain relatively immobile while undergoing the treatment.

In view of the above disadvantages, there exists a need for a therapeutic wrap that increases the length of time of the therapeutic treatment while remaining portable in addition to applying the therapeutic effect to the appropriate anatomical area.

SUMMARY OF THE INVENTION

The present invention disclosed and claimed herein comprises a therapeutic wrap for disposal about an anatomical surface. The wrap includes an outer wrapping layer having first and second ends with the first end operable to be placed over the second end. The inner side of the wrap is operable to be disposed adjacent the treatment area and an outer side for being disposed outward therefrom. A first inner pocket is disposed on the inner side of the wrap a predetermined distance away from the first end, the first pocket having a width of x. A second inner pocket is disposed on the inner side of the wrap adjacent the first inner pocket diametrically opposite the first end and having a width of x. A third inner pocket is disposed on the inner side of the wrap adjacent the second pocket and diametrically opposite the first pocket. First, second and third gels are provided for being removably disposed in the first, second and third pockets, respectively. A first attachment strip is disposed adjacent the inner side of the outer wrap proximate the first end and then extending inward from the first end toward the first pocket. A second attachment strip for being removably mated with a first attachment strip is disposed adjacent the outer side of the outer wrap proximate the second end and extending from the second end inward toward the third pocket and adjacent the third pocket. The dimension x is such that the outermost first and third pockets are disposed against the medial and lateral sides of the knee of an average adult. The gel packs can then be disposed in the first and third pockets to provide a therapeutic treatment therefor. The second free end of the outer wrap being of a dimension 2x is such that it will fold over itself once and then over the third pocket if the third pocket does not have a gel pack disposed therein. In this configuration, the dimension x facilitates disposal about an elbow or an ankle and covers the medial and lateral sides thereof.

In another embodiment of the invention, the outer wrapping layer is comprised of a layer of reflective material over which a fibrous material is disposed. The reflective material reflects heat, thus preventing heat transfer from the outside of the wrap to the inside thereof.

BRIEF DESCRIPTION OF THE DRAWING

For a more complete understanding of the present invention and the advantages thereof, reference is now made to the following description taken in conjunction with the accompanying Drawings in which:

FIG. 1 illustrates a perspective view of the material used for the therapeutic wrap in accordance with the present invention;

FIG. 2 illustrates a perspective view of a therapeutic wrap for disposal about the limbs;

FIG. 3 illustrates a cross-sectional view taken along lines 3—3 of FIG. 2;

FIGS. 4a–4d illustrate the operation of the multi-pocketed wrap and the spacial relationship of the pockets;

DETAILED DESCRIPTION OF THE INVENTION

Figures 5A, 5B, 5C:
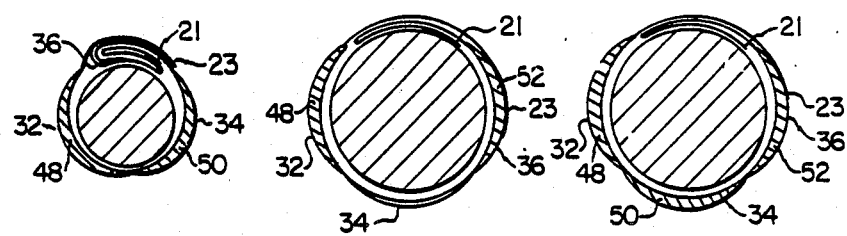
FIGS. 5a–5c illustrate cross-sectional views of the wrap disposed on various limbs.

Referring now to FIG. 1, there is illustrated a perspective view of a section of multilayered cloth 10. The multilayered cloth 10 is comprised of a layer of water repellant material 12, a layer of highly efficient (80% or better) thermally reflective material 14 and a layer of insulating material 16. The layer of water repellant material 12 is fabricated from 100% nylon with an Enduracote finish which is an extra-heavy duty urethane coating that seals the fabric against water and wear, yet provides breathability to allow moisture to escape.

The thermally reflective layer 14 is functional to reflect heat from one side thereof. In this manner, an effective radiant heat insulator is provided which both prevents heat from being transmitted thereacross and also reflects the heat back toward the thermal source. In the preferred embodiment, the thermally reflective layer 14 is fabricated from a highly thermally reflective material such as aluminized polyester film with a layer of fiberglass scrim attached thereto to provide strength. The thermal layer is approximately 0.0005 inch and the layer of fiberglass scrim is configured as a mesh which is attached to one side thereof. This scrim layer provides a high degree of tear strength. In the preferred embodiment, the thermally reflective layer is laminated to a layer of vinyl having a thickness of approximately 0.003 inches with the layer of scrim disposed therebetween. The opposite side of the thermally reflective film faces the insulating layer 16 and the laminated side faces the water repellant layer 12. In the preferred embodiment, the material utilized for the thermally reflective layer 14 is of the type such as Astrolon VIII manufactured by Metalized Products, Winchester, Mass.

The layer of insulating material 16 disposed adjacent the thermally reflective side of the layer 14 is, in the preferred embodiment, fabricated from a woven cloth. This layer is operable to prevent contact of an external surface with the surface of the thermally reflective layer 14. This introduces a relatively high thermal resistance between an external surface and the surface of the thermally reflective layer 14 such that transmission of heat by thermal conduction is minimized. Therefore, the effectiveness of a radiant reflector is increased. In the preferred embodiment, the insulating layer 16 is fabricated from a flannel layer having a weight of approximately seven ounces which, as described above, has a relatively high thermal resistance.

Referring now to FIG. 2 there is illustrated a perspective view of a thermal wrap 18 in accordance with the present invention. The wrap 18 has an external side 20 and an internal side 22. The internal side 22 corresponds to the insulating layer 16 and the side 20 corresponds to the water repellant side 12 of the section 10. The thermally reflective layer 14 is disposed between the external side 20 and the internal side 22.

A layer 24 and a layer 26 of fibrous material are disposed on the external side 20 proximate an end 21 of the wrap 18. A layer 28 and a layer 30 of hook-like material are disposed on the interior side 22 proximate an end 23 of the wrap 18 diametrically opposite the end 21 to which the layers 24 and 26 are attached. The layers 28 and 30 are operable to mate with the layers 24 and 26, respectively, to provide an attachment therebetween, as will be described hereinbelow. When the wrap 18 is disposed about an injured limb, the hook-like material of the layers 28 and 30 intertwine with the fibrous material 24 and 26, thus providing resistance to forces directed parallel to the plane of the surfaces. However, separation can be accomplished by applying a separation force perpendicular to both surfaces. The material forming the layers 24, 26, 28 and 30 is commonly referred to as Velcro.

The strips 24 and 26 are disposed about the periphery of the wrap 18 on the external side 20 to allow adjustability of the wrap 18. In this manner, the wrap 18 can be disposed around an injured limb and tightened before attaching the strips 28 and 30 thereto. Since the attachment provided by the strips 24, 26, 28 and 30 is resistant to lateral forces, the wrap 18 should remain in place until manually separated by an external force. This provides a great deal of pullability for the wrap 18. To further secure the wrap 18, a peripheral strap 31 is applied around the wrap and mates with a buckle (D-ring) 33 for insertion therethrough to allow the strap 31 to be tightened. The strap 31, when tightened, functions to apply pressure to the injured limb.

A pocket 32, a pocket 34, and a pocket 36 are formed by disposing an additional layer of insulating material adjacent the interior surface 22. The additional layer of insulating material has a seam 38 formed along the bottom edge thereof and vertical seams 40 and 42 formed along opposite sides thereof. The top side remains open. A vertical seam 44 is sewn to provide separation between the pockets 32 and 34 and a vertical seam 46 defines the boundaries between the pockets 34 and 36. A gel pack 48 is removably disposed in the pocket 32, a gel pack 50 is removably disposed in the pocket 34 and a gel pack 52 is removably disposed in the pocket 36.

The gel packs 48-52 are fabricated from a material that has a relatively high specific heat. Normally these are fabricated from some form of liquid having the same boiling point and the same freezing point as water. The liquid is encased in a sealed plastic container such that they are reusable. The gel packs 48-52 are disclosed in U.S. Pat. No. 3,780,537, which is incorporated herein by reference.

By predisposing the gel packs 48-52 in either a high temperature environment or a low temperature environment, heat can either be applied to an adjacent surface or extracted therefrom. By removing one of the gel packs 48-52, as will be described hereinbelow, the therapeutic effect can be decreased.

To secure the open ends of the pockets 32-36, a Velcro securing material is utilized. This material is comprised of a square shaped layer 55 of hook-like material disposed on the internal 22 and a square shaped layer 57 of fibrous material disposed on the inner surface of the associated one of the pockets 32-36 proximate the opening hereof. Pressing together of these two layers firmly secures the gel pack in the respective pocket.

Referring now to FIG. 3 which illustrates a cross-sectional view taken along line 3—3 of FIG. 2, the operation of the therapeutic wrap 18 with the multi-layered material will be described in more detail. As described above, the insulating layer 16 forms the inner internal side 22 of the wrap 18. When the gel pack 48 is disposed in the pocket 36, one side thereof is adjacent the layer of insulating material 16. The layer of insulating material 16 is functional to provide an airspace between the outer surface of the gel pack 48 and the thermally reflecting layer 14. In this manner, heat radiated from the opposite side of the wrap 18 is reflected back to an anatomical surface. Essentially, a very high thermal resistance is provided between the gel pack 48 and the external environment of the wrap 18. As described above, it is important to prevent the gel pack 48 from making direct contact with the thermally reflecting layer 14 to reduce the heat transfer by conduction. Therefore, heat transfer between the external environment and the gel pack 48 is substantially reduced.

The material that forms the pocket 36, as described above, is also fabricated from a material that is of the same insulating material as layer 16. This layer of material functions to provide an airspace between the anatomical surface that the wrap 18 is disposed about and the gel pack 48. This airspace increases the thermal resistance between the two surfaces, thus reducing the heat transfer therebetween. By increasing the thermal resistance, the rate of heat transfer to the anatomical surface is decreased, thereby increasing the time that the gel pack 48 will maintain an effective temperature gradiant. For example, if a gel pack 48 is chilled to a temperature 40° below the skin surface of the area to be treated, direct contact between the two surfaces may be detrimental. By disposing the material of the pocket 36 therebetween, the rate of heat extraction from the anatomical surface is controlled, thus allowing a longer period of time for the overall therapeutic effect. Since heat transfer from the external environment is substantially reduced by the thermally reflective layer 14, all heat transfer occurs from the anatomical surface to the gel pack 48. The length of time that the gel pack 48 will maintain a lower or higher temperature external to the anatomical surface depends upon the thermal capacity of the gel pack 48, the initial temperature thereof, and the thermal resistance of the layer of material between the gel pack 48 and the anatomical surface. Although the temperature of the gel pack 48 is maintained below the surface temperature of the anatomical surface in the above example, it should be understood that the gel pack 48 can be maintained at a higher temperature than the anatomical surface, depending upon the particular therapeutic effect desired.

Referring now to FIGS. 4a–4d, there are illustrated various views showing how the pockets 32-36 are arranged and how they are specially dimensioned with respect to each other. Each of the pockets 32-36 has an equal width which is referred to as "x". The end 21 is 2x-long with the end 23 being approximately the same length.

When three gel packs 48, 50 and 52 are utilized, the x-dimension is such that the wrap will be disposed about a limb with the end 23 overlapping the end 21 and the strip 30 adhering to the strip 26. However, it is important to note that the end 21 does not overlap any of the pockets 32-36 or, if so, the overlapping is minimal. Therefore, the dimension "x" is selected such that the largest limb to be treated will have a diameter wherein the end 23 overlaps the end 21. If a smaller limb is to be treated, the distal x-length and the x-length adjacent thereto can be folded over, as illustrated in FIG. 4b, to provide a shorter distance. The end 23 can then be overlapped and attached to the portion of the strips 26 on the end 21 which were not folded over. This will allow all three gel packs 48-52 to be in contact with the limb without requiring the end 21 or any portion thereof overlapping with any of the pockets 32-36.

If a smaller limb is to be treated, the gel pack 52 is removed from pocket 36 and the 2x-length of the end 21 folded over the x-length of pack 32. This step is illustrated in FIG. 4c. The next step (now shown) is to fold the end 21 again such that it does not overlap the pocket 34. The end 23 is then placed over the exterior side of the pocket 32 and the strips 30 and 26 adhered thereto to accommodate the smaller limb. With this configuration, the end 21 still does not overlap or in any way impede thermal transfer between the gel packs 48 and 50 and the limb to be treated.

Another configuration is illustrated in FIG. 4d with the gel pack 52 removed from pocket 36. The end 21 is first overlapped over itself such that it is "x" long. It is then folded over the x-length of the pocket 36. This provides a surface having a width of "x" as opposed to the configuration of FIG. 4c, which has a width equal to 1.50x.

Referring now to FIGS. 5a–5c, there is illustrated cross-sectional views of various diameter limbs about which the wrap 18 is disposed. With particular reference to FIG. 5a, the gel packs are disposed only in pockets 32 and 34 since the illustrated limb is a rather small dimension such as an elbow or an ankle. As can be seen, the gel packs 48 and 50 are disposed medial and laterally about the limb providing relatively full coverage over those particular portions of the limb.

Normally, therapeutic heat or cold treatment is required on localized areas. These are normally concentrated on medial and lateral side of limbs since most tendons and adjacent musculature enters the joint and passes therethrough proximate dorsal and ventral sides. Therefore, there is a minimum amount of tissue on the medial and lateral side of most joints. For example, in the elbow the two condyler of the humerus extend medially and laterally with the musculature and ligaments extending therearound. The synovial membrane protrudes outward in some areas and, at some angles of extension, is slightly exposed. The ligaments that are proximate the joint adjacent the medial and lateral sides can become stretched and the membrane swollen. Heat treatment is generally recommended for the medial and lateral sides. This is facilitated with the arrangement of FIG. 5a.

Referring now to FIG. 5b, there is illustrated an arrangement about a larger limb such as a knee. The arrangement of FIG. 5b illustrates the use of the gel packs 48 and 52 in pockets 32 and 36, respectively. The gel pack 50 is removed from the pocket 34. In this manner, the gel packs are only disposed on the lateral sides of the member. This facilitates bending of the joint since neither the dorsal or the ventral sides of the joint are impeded. Thermal treatment has been provided for only the lateral side in which movement is not present.

Referring to FIG. 5c, there is illustrated an arrangement for a joint such as a knee where all three gel packs 48-52 are disposed in the pockets 32-36, respectively. This allows the medial and lateral sides to be treated in addition to the underside of the knee. The selective placement of gel packs allows an individual to provide the therapeutic heat or cold treatment to only those areas that are necessary. This is an advantage in that unnecessary application of heat or cold makes the wrap somewhat bulky whereas selective removal of the pads can significantly improve mobility while wearing the pad. For example, the arrangement of FIG. 5b allows the knee to bend if the pads are only disposed adjacent the medial and lateral sides thereof. In addition, the relationship between the pads for a three pocket system not only allows selective removal of the pads but it also accommodates the majority of the limbs on individuals from a child to a large adult.

Figure 6:
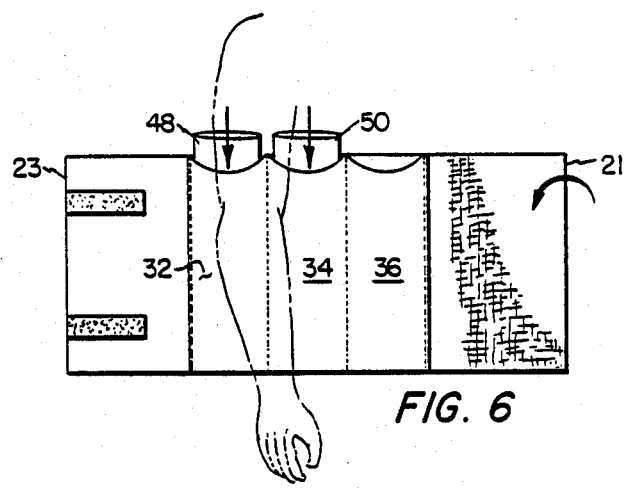
FIG. 6 illustrates the wrap being disposed about the elbow.

Referring now to FIG. 6, there is illustrated a top view of the wrap 18 being disposed about the elbow. Since the elbow is smaller, the gel pack 52 is removed from the pocket 36. The end 21 is then folded over the pocket 36 and then again over itself. The end 23 is then folded over the folded configuration of end 21 and pocket 32. This is similar to the cross sectional view of FIG. 5a. This configuration would also be used for the wrist or the ankle or for the knee on a child. In this configuration, the elbow can still bend as the seam between the pockets 34 and 36 is disposed at the joint along the midline thereof. The folded end is adjacent the upper side of the elbow such that it can bend relatively easy.

Figure 7:
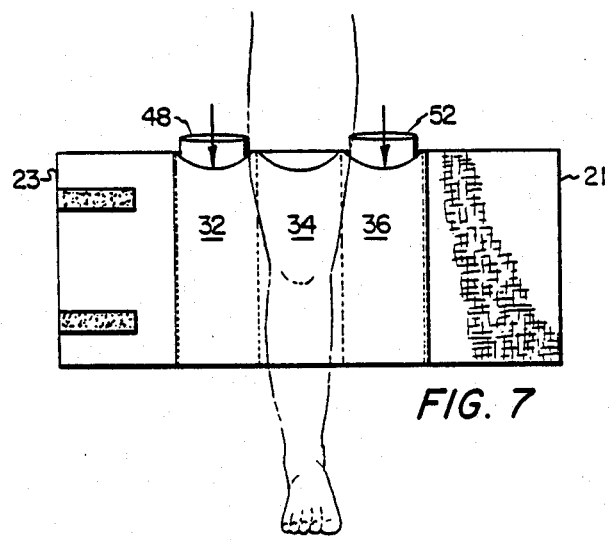
FIG. 7 illustrates the wrap being disposed about the knee.

Referring now to FIG. 7, there is illustrated a top view of the wrap 18 for being disposed about a larger limb or joint such as the knee. For this configuration, which corresponds to the configuration of FIG. 5b, the gel pack 50 is removed from the pocket 34. The knee is then placed with the underside down against the pocket 34 and the portion 21 folded over and placed on top of the knee cap. The end portion 23 is then overlapped over the folded portion 21 to secure the wrap 18 about the knee. If the wrap were moved upwards against the thigh of a large individual, the portion 20 would not have to be folded over, as a larger diameter would be incurred.

The dimension "x" is approximately 5.0 inches. This allows the pocket with the gel pack disposed therein to extend from the medial side of the average adult elbow or ankle to the lateral side thereof. This would allow pockets 32 and 34 to provide medial and lateral treatment for either an elbow or ankle on the average adult. The average adult's knee, on the other hand, is approximately 9.5 inches from the medial side to the lateral side. By utilizing pockets 32 and 36, the midpoint dimension is approximately 10 inches between the two pockets such that medial and lateral treatment is effected on the knee.

In summary, there has been provided a therapeutic wrap with three pockets. The pockets are disposed such that two adjacent pads provide medial and lateral treatment for a small limb such as an adult's elbow or gel packs can be disposed in the pockets and the two outermost pockets to provide medial and lateral treatment for larger limbs such as a knee. One end of the wrap is designed to fold over such that it does not overlap the treatment area and reduce the thermal effect of the gel pack.

Although the preferred embodiment has been described in detail, it should be understood that various changes, substitutions and alterations can be made therein without departing from the spirit and scope of the invention as defined by the appended claims.

What is claimed is:

1. A therapeutic wrap, comprising:
   an outer wrapping having first and second end portions and a middle portion, said first end portion operable to be placed over said second end portion, said outer wrap having an innerside thereof for being disposed against a treatment area on a patient and an outer side thereof for being disposed outward therefrom, said outer wrapping being fabricated of an insulated material;
   a first inner pocket disposed on the innerside of said outer wrap on said middle portion adjacent said first end portion, said first inner pocket having a given width;
   a first gel pack for being disposed in said first inner pocket;
   a second inner pocket disposed on said middle portion adjacent said first inner pocket on the inner side of said outer wrap diametrically opposite said first inner pocket from said first end, said second inner pocket being of a width equal to said given width;
   a second gel pack for being disposed in said second inner pocket;
   a third inner pocket disposed on said middle portion adjacent said second inner pocket diametrically opposite said first inner pocket on the inner side of said outer wrap and adjacent said second end portion, said third inner pocket having a width equal to said given width;
   a third gel pack for being disposed in said third inner pocket;
   said first, second and third gel packs for being disposed at a hot or cold temperature to provide a therapeutic treatment;
   said given width being approximately equal to the medial to lateral distance for an average adult's elbow;
   a first attachment strip having first and second ends with said first attachment strip attached to the inner side of said outer wrap adjacent said first end portion and extending inward from said first end portion toward said first inner pocket;
   a second attachment strip for removably adhering to said first attachment strip and disposed on the outer side of said outer wrap proximate said second end portion and extending inward from said second end portion toward said third inner pocket and adjacent said third inner pocket;
   said second end portion having a width equal to twice said given width such that it can fold over on itself to prevent overlapping with the inner side of said first, second and third inner pockets when wrapped about a joint, and can overlap again with said third pocket when said third gel pack is not disposed therein and the diameter of the joint is such that said first end extends over said third pocket and said first end portion having a width equal to twice said given width.

2. The therapeutic wrap of claim 1 wherein said outer wrapping is fabricated from a high specific heat material functional to maintain a temperature gradient between said outer layer and the anatomical surface enclosed thereby.

3. The therapeutic wrap of claim 1 wherein said gel pack comprises a gel disposed in a flexible sealed envelope and having a boiling point equal to water and a freezing point equal to water.

4. The therapeutic wrap of claim 1 said given width is approximately five inches.

5. The therapeutic wrap of claim 1 and further comprising a peripheral strap for being disposed on the outer surface of said outer wrapping with first and second free ends, the first and second ends being attachable to each other to allow said peripheral strap to be pulled tight about the limb.

6. The therapeutic wrap of claim 1 wherein said insulating layer comprises:
   a layer of thermally reflecting material; and
   a layer of insulating material disposed adjacent to said thermally reflecting layer.

7. The therapeutic wrap of claim 6 and further comprising a layer of water repellant material disposed adjacent said layer of thermally reflecting material opposite said insulating layer, said water repellant layer forming the exterior of the therapeutic wrap when disposed about the anatomical surface.

8. The therapeutic wrap of claim 6 wherein said thermally reflecting layer comprises aluminized polyester.

9. The therapeutic wrap of claim 6 wherein said insulating layer comprises a woven material.

* * * * *